United States Patent [19]

Cross et al.

[11] Patent Number: 5,233,053

[45] Date of Patent: Aug. 3, 1993

[54] PYRROLIDINE DERIVATIVES

[75] Inventors: Peter E. Cross, Canterbury; Alexander R. MacKenzie, Deal, both of England

[73] Assignee: Pfizer Inc., New York, N.Y.

[21] Appl. No.: 800,191

[22] Filed: Feb. 7, 1992

Related U.S. Application Data

[62] Division of Ser. No. 491,068, Mar. 13, 1990, Pat. No. 5,096,890.

[30] Foreign Application Priority Data

Mar. 17, 1989 [GB] United Kingdom ............... 8906166

[51] Int. Cl.$^5$ .................. C07D 207/09; C07D 207/10
[52] U.S. Cl. ..................................... 548/568; 548/567
[58] Field of Search ................ 548/567, 568; 514/422

[56] References Cited

U.S. PATENT DOCUMENTS 4,002,766 1/1977 Welstead ........................... 514/408

FOREIGN PATENT DOCUMENTS 178946 4/1986 European Pat. Off. .

Primary Examiner—C. Warren Ivy
Assistant Examiner—Celia Chang
Attorney, Agent, or Firm—Peter C. Richardson; Paul H. Ginsburg; Seymour G. Bekelnitzky

[57] ABSTRACT

Compounds of the formula

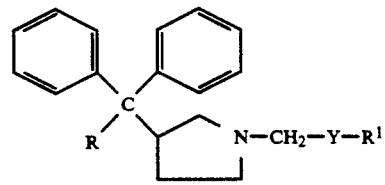

wherein R, Y and $R^1$ are as defined in the specification. These compounds are muscarinic receptor antagonists which are selective for smooth muscle muscarinic sites over cardiac muscarinic sites, and are useful in the treatment of diseases associated with altered motility on tone of smooth muscle, including irritable bowel syndrome, diverticular disease, urinary incontinence, oesophageal achalasia and chronic obstructive airways disease.

1 Claim, No Drawings

PYRROLIDINE DERIVATIVES

This is a division of application Ser. No. 07/491,068, filed on Mar. 13, 1990, now U.S. Pat. No. 5,096,890.

BACKGROUND OF THE INVENTION

This invention relates to certain 3-substituted pyrrolidine derivatives. The compounds of the invention are muscarinic receptor antagonists which are selective for smooth muscle muscarinic sites over cardiac muscarinic sites and which do not have any significant antihistamine activity. Thus the compounds are useful in the treatment of diseases in mammals, including humans, associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

SUMMARY OF THE INVENTION

According to the invention there are provided compounds of the formula:

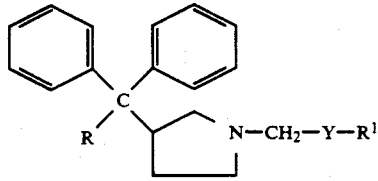

(I)

wherein
Y is a direct link, —CH$_2$—, —(CH$_2$)$_2$—, —CH$_2$O— or —CH$_2$S—;
R is —CN or —CONH$_2$;
and
R$^1$ is a group of the formula:

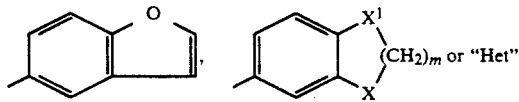

where
X and X$^1$ are each independently O or CH$_2$;
m is 1, 2 or 3;
and
"Het" is pyridyl, pyrazinyl or thienyl.

R is preferably —CONH$_2$. The compounds in which R is CN have some activity as muscarinic receptor antagonists but are mainly useful as synthetic intermediates.

m is preferably 1.
R$^1$ is preferably

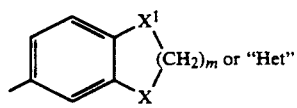

where X, X$^1$, m and "Het" are as defined for formula (I).

R$^1$ is more preferably:

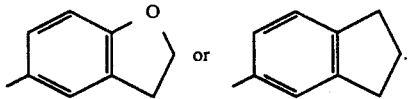

Y is preferably a direct link or —CH$_2$—.
Y is most preferably —CH$_2$—.
"Het" is preferably pyridyl.

The anticholinergic activity of the present compounds resides in both the 3R-forms and 3S-forms, i.e., the compounds having R and S stereochemistry, respectively, at position 3 of the pyrrolidine ring, and of course in the 3R,S-(racemic) forms of the compounds (I). The 3S- forms are generally the most active.

The pharmaceutically acceptable salts of the compounds of formula (I) include acid addition salts such as the hydrochloride, hydrobromide, hydrofluoride, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1-19. These salts can be prepared conventionally, e.g. by mixing a solution of the free base and the acid in a suitable solvent, e.g. ethanol, and recovering the acid addition salt either as a precipitate, or by evaporation of the solution.

DETAILED DESCRIPTION OF THE INVENTION

The compounds of the formula (I) can be prepared by a number of routes, including the following:

Route A

This can be illustrated as follows:

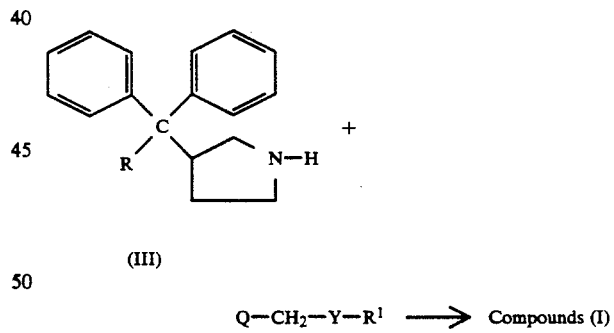

Y, R and R$^1$ are as defined for formula (I) and Q is a leaving group, e.g. Br, Cl, I, C$_1$-C$_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium or potassium carbonate or bicarbonate, triethylamine or pyridine, and in a suitable organic solvent, e.g. acetonitrile, at up to the reflux temperature. Reaction temperatures of 60°-105° C. are usually desirable and it is generally convenient to carry out the reaction under reflux, although in some instances the reaction may proceed at a suitable rate at room temperature. Iodo is often a particularly suitable leaving group but since the starting materials (III) are sometimes most conveniently available as chlorides the reaction can also be carried out using the compound (III) as a chloride but in the presence of an iodide such as sodium or potassium iodide. In the preferred technique, the compounds (II) and (III) are refluxed together in acetonitrile in the presence of potassium carbonate or sodium bicarbonate. The product (I) can be isolated and purified conventionally.

The 3R,S-, 3R- or 3S- forms of the starting material (II) can be used so as to obtain the 3R,S-, 3R- or 3S- forms, respectively, of the product (I).

The starting materials of the formula (II) can be obtained by conventional procedures such as those described in the following Preparations. The starting materials of the formula (III) are in general known compounds which can be prepared by conventional techniques. The preparation of any novel starting materials of the formula (III) used in the Examples is however described in the following Preparations section.

Route B

The compounds of the formula (I) in which R is —CONH$_2$ can also be prepared by the hydrolysis of the corresponding nitriles, e.g. using concentrated aqueous mineral acid (typically concentrated aqueous H$_2$SO$_4$).

The hydrolysis is typically carried out using concentrated aqueous sulphuric acid, preferably 80-98% sulphuric acid and most preferably 95% H$_2$SO$_4$, with heating at e.g. 70°-110° C. The product can then be isolated and purified by conventional procedures.

Route C

This route is useful for preparing compounds in which Y is —CH$_2$— and R$^1$ is 2- or 4-pyridyl or pyrazinyl and can be represented as follows:

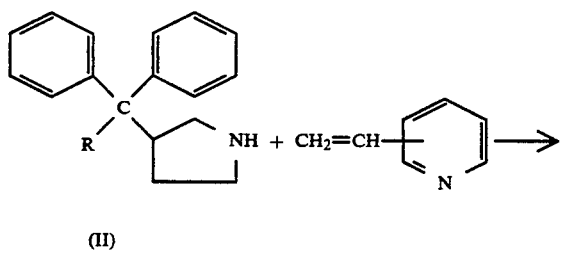

(II)

or

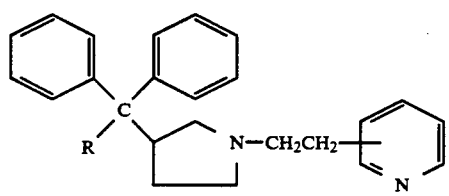

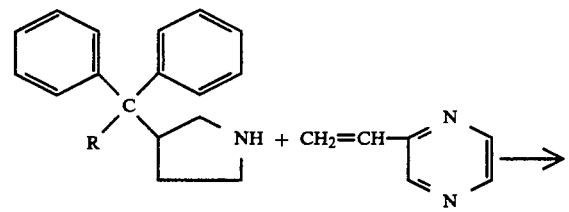

(II)

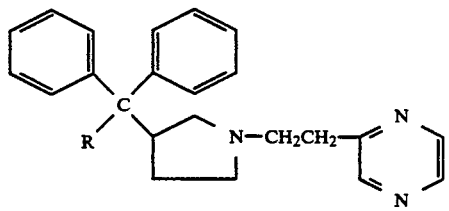

R is as defined for formula (I). Clearly the vinyl group must be attached to the 2- or 4-position of the pyridine ring.

The reaction is typically carried out with heating, e.g. at about 60° to 110° C. and preferably under reflux, in a suitable organic solvent, e.g. dioxan. In some instances, the use of a basic (preferably a strong base which is soluble in an organic solvent such as N-benzyltrimethylammonium hydroxide ["Triton B"]) or acidic (preferably a C$_1$-C$_4$ alkanoic acid) catalyst may be beneficial.

Route D

Compounds of the formula (I) in which R is —CONH$_2$ and R$^1$ is a group of the formula:

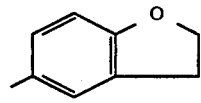

can be prepared by the reduction of the corresponding compounds of the formula (I) in which R$^1$ is a group of the formula:

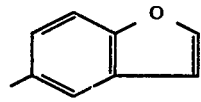

The reduction can be carried out conventionally, e.g., by hydrogenation or by using stannous chloride, tributyltin hydride or a trialkysilane (e.g. triethylsilane).

The preferred technique is catalytic hydrogenation, typically using H$_2$/Pd/C at from about atmospheric pressure up to about 60 psi (413.6 kPa) in a suitable solvent, e.g. acetic acid.

Route E

This route, which prepares a compound of the formula (I) in which R is —CONH$_2$, Y is —CH$_2$— and R$^1$ is 2,3-dihydrobenzofuran-5-yl or indan-5-yl, involves the reduction of a compound of the formula:

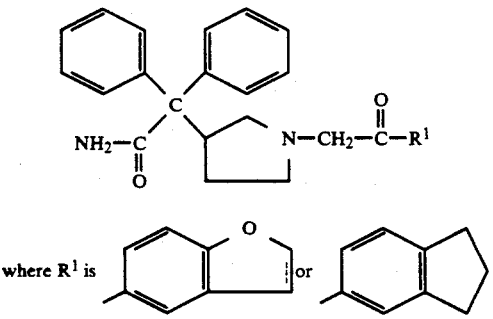

(IV)

where $R^1$ is where the dotted line represents an optional bond.

The reduction can be carried out similarly to Route D above. When the dotted line represents a bond, the reduction will reduce both the carbonyl group and the double bond in the 2,3-position of the benzofuran-5-yl group.

The preferred technique is again catalytic hydrogenation (e.g. using $H_2/Pd/C$) in a suitable solvent, e.g. acetic acid, and preferably under a hydrogen pressure of 40-60 psi (275.7 to 413.6 kPa). The starting materials (IV) can be prepared by conventional techniques such as those illustrated in Preparations 18 and 19.

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1-5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined ($pA_2$ value-Arunlakshana and Schild (1959), Brit. J. Pharmacol., 14, 48-58). Using the above analytical techniques, tissue selectively for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes the novel intermediates of the formula (II), particularly those in the 3R,S-(racemic) and 3S-forms, and the novel intermediates of the formula (IV).

The following Examples illustrate the invention:

EXAMPLE 1

(A) Preparation of
3-(R,S)-(1-carbamoyl-1,1-diphenylmethyl)-1-[2-(2,3-dihydrobenzofuran-5-yl)ethyl]pyrrolidine

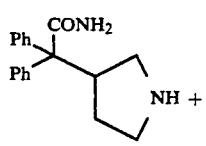

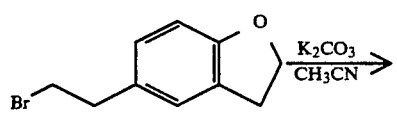

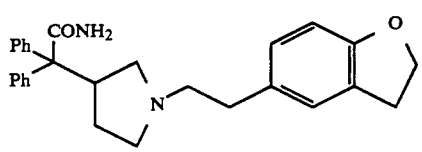

A mixture containing 3-(R,S)-(1-carbamoyl-1,1-diphenylmethyl)pyrrolidine (0.33 g-see Preparation 8), 5-(2-bromoethyl)-2,3-dihydrobenzofuran (0.25 g-see Preparation 13), anhydrous potassium carbonate (0.3 g) and acetonitrile (10 ml) was heated under reflux for 2 hours. The mixture was partitioned between dichloromethane (50 ml) and 10% aqueous potassium carbonate (10 ml), the layers were separated, and the aqueous layer extracted with dichloromethane (3×20 ml). The combined dichloromethane extracts were dried (MgSO$_4$) and concentrated in vacuo to leave a gum which was purified by column chromatography on silica eluting with dichloromethane containing methanol (0% up to 8%). The product-containing fractions were combined and concentrated in vacuo to leave an oil which was crystallised from diisopropyl ether to give the title compound as a colourless powder, yield 0.17 g, m.p. 131°–132° C.

Analysis %:

Found: C,78.90; H,7.70; N,6.28;

Calculated for C$_{28}$H$_{30}$N$_2$O$_2$: C,78.84; H,7.90; N,6.57.

$^1$H N.m.r. (CDCl$_3$) δ=7.50–7.20 (m, 11H); 7.00 (s, 1H); 6.90 (d, 1H); 6.70 (d, 1H); 5.45–5.30 (brs, 1H); 4.60–4.50 (t, 2H); 3.60–3.45 (m, 1H); 3.25–3.15 (t, 2H); 3.05–2.50 (m, 8H); 2.10–1.95 (m, 2H) ppm.

(B) A similar procedure starting with 3-(S)-(−)-(1-carbamoyl-1,1-diphenylmethyl)pyrrolidine (1.95 g - see Preparation 10(B)) gave 3-(S)-(−)-(1-carbamoyl-1,1-diphenylmethyl)-1-[2-(2,3-dihydrobenzofuran-5-yl)ethyl]pyrrolidine as a foam, yield 1.9 g, [α]$_D^{25}$ −20.6° (c 1.0, CH$_2$Cl$_2$).

(C) A similar procedure starting with 3-(R)-(+)-(1-carbamoyl-1,1-diphenylmethyl)pyrrolidine (2.8 g - see Preparation 11) gave 3-(R)-(+)-(1-carbamoyl-1,1-diphenylmethyl)-1-[2-(2,3-dihydrobenzofuran-5-yl)ethyl]pyrrolidine as a foam, yield 1.7 g, [α]$_D^{25}$ +18.1 (c 1.0, CH$_2$Cl$_2$).

EXAMPLE 2

(A) Preparation of
3-(R,S)-(1-carbamoyl-1,1-diphenylmethyl)-1-[2-(indan-5-yl)ethyl]pyrrolidine

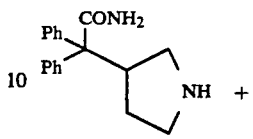

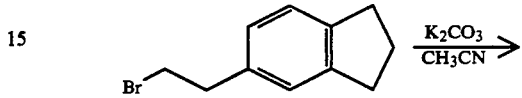

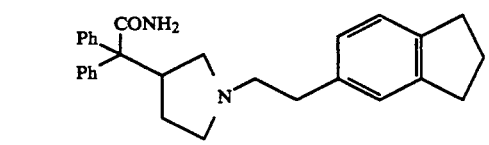

A mixture containing 3-(R,S)-(1-carbamoyl-1,1-diphenylmethyl)pyrrolidine (0.6 g-see Preparation 8), 5-(2-bromoethyl)indane (0.49 g-see Preparation 14), anhydrous potassium carbonate (0.6 g) and acetonitrile (20 ml) was heated under reflux for 1.25 hours. The mixture was partitioned between 10% aqueous potassium carbonate (10 ml) and dichloromethane (50 ml), the layers were separated and the aqueous layer extracted with dichloromethane (3×100 ml). The combined dichloromethane extracts were dried (MgSO$_4$) and concentrated in vacuo to give a gum which was purified by column chromatography on silica eluting with dichloromethane containing methanol (0% up to 6%). The product-containing fractions were combined and concentrated in vacuo to give the title compound as a foam, yield 0.29 g.

Analysis %:

Found: C,80.59; H,7.99; N,6.11;

Calculated for C$_{29}$H$_{32}$N$_2$O.½H$_2$O: C,80.33; H,7.67; N,6.46.

$^1$H N.m.r. (CDCl$_3$), δ=8.00–7.70 (brs, 1H); 7.50–7.20 (m, 10H); 7.15 (d, 1H); 7.05 (s, 1H); 6.95 (d, 1H); 5.45–5.30 (brs, 1H); 3.55–3.40 (m, 1H); 3.00–2.60 (m, 12H); 2.60–2.40 (m, 1H); 2.15–1.90 (m, 3H) ppm.

(B) A similar procedure starting with 3-(S)-(−)-(1-carbamoyl-1,1-diphenylmethyl)pyrrolidine (0.64 g-see Preparation 10(B)) gave 3-(S)-(−)-(1-carbamoyl-1,1-diphenylmethyl)-1-[2-(indan-5-yl)ethyl]pyrrolidine, yield 0.34 g, [α]$_D^{25}$ −10.4° (c 1.0, CH$_2$Cl$_2$).

EXAMPLE 3

Preparation of
3-(R,S)-(1-carbamoyl-1,1-diphenylmethyl)-1-(3,4-methylenedioxybenzyl)pyrrolidine

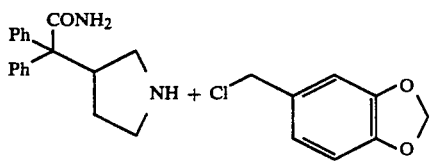

-continued

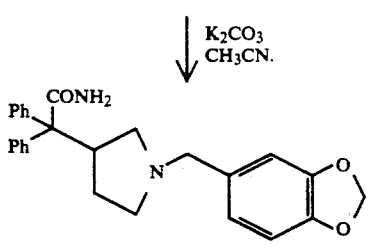

A mixture containing 3-(R,S)-(1-carbamoyl-1,1-diphenylmethyl)pyrrolidine (0.75 g-see Preparation 8), 3,4-methylenedioxybenzyl chloride (0.51 g-commercially available), anhydrous potassium carbonate (0.75 g) and acetonitrile (30 ml) was stirred at room temperature for 30 minutes. The mixture was partitioned between 10% aqueous potassium carbonate (20 ml) and dichloromethane (50 ml), the layers were separated and the aqueous layer extracted with dichloromethane (3×50 ml). The combined dichloromethane extracts were dried (MgSO$_4$) and concentrated in vacuo to give a foam which was purified by column chromatography on silica eluting with dichloromethane containing methanol (0% up to 10%). The product-containing fractions were combined and concentrated in vacuo to give the title compound as a foam, yield 0.5 g.

Analysis %
Found: C, 74.15; H, 6.26; N, 6.56;
Calculated for $C_{26}H_{26}N_2O_3.\tfrac{1}{4}H_2O$: C, 74.53; H, 6.38; N, 6.69.

$^1$H N.m.r. (CDCl$_3$), δ=7.45-7.20 (m, 11H); 6.80-6.65 (m, 3H); 5.95 (s, 2H), 5.60-5.50 (brs, 1H); 3.60-3.40 (m, 3H); 2.90-2.70 (m, 2H); 2.70-2.55 (m, 1H); 2.50-2.40 (m, 1H); 2.05-1.90 (m, 2H) ppm.

EXAMPLE 4

Preparation of 3-(R,S)-(1-carbamoyl-1,1-diphenylmethyl)-1-[2-(3,4-methylenedioxyphenyl)ethyl]pyrrolidine

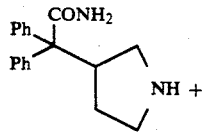

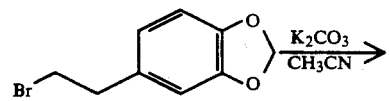

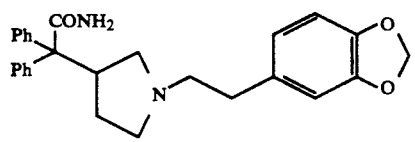

A mixture containing 3-(R,S)-(1-carbamoyl-1,1-diphenylmethyl)pyrrolidine (0.3 g -see Preparation 8), 3,4-methylenedioxyphenethyl bromide (0.247 g -see Preparation 16), anhydrous potassium carbonate (0.4 g) and acetonitrile (10 ml) was heated under reflux for 3 hours. The mixture was allowed to cool to room temperature, water (6 ml) was added and the mixture was extracted with dichloromethane (3×50 ml). The combined dichloromethane extracts were dried (MgSO$_4$) and concentrated in vacuo to give a colourless foam which was purified by column chromatography on silica eluting with dichloromethane containing methanol (0% up to 6%). The product-containing fractions were combined and concentrated in vacuo to give the title compound as a colourless foam, yield 0.27 g.

Analysis %:
Found: C, 73.44; H, 6.46; N, 6.62;
Calculated for $C_{27}H_{28}N_2O_3.\tfrac{1}{4}CH_2Cl_2$: C, 73.69; H, 6.48; N, 6.29.

$^1$H N.m.r. (CDCl$_3$) δ=7.80-7.60 (brs, 1H); 7.50-7.15 (m, 10H); 6.75-6.60 (m, 3H); 5.95 (s, 2H); 5.45-5.35 (brs, 1H); 3.55-3.40 (m, 1H); 3.00-2.40 (m, 8H); 2.10-1.90 (m, 2H) ppm.

EXAMPLE 5

Preparation of 3-(R,S)-(1-carbamoyl-1,1-diphenylmethyl)-1-[2-(2-pyridinyl)ethyl]pyrrolidine

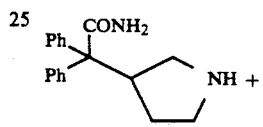

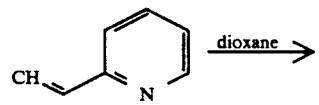

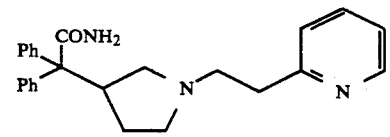

A mixture containing 3-(R,S)-(1-carbamoyl-1,1-diphenylmethyl)pyrrolidine (1.0 g-see Preparation 8), 2-vinylpyridine (0.5 g) and 1,4-dioxane (10 ml) was heated under reflux for 20 hours. On cooling to room temperature the mixture was filtered and the filtrate was diluted with water (100 ml) then extracted with dichloromethane (3×50 ml). The combined dichloromethane extracts were dried (MgSO$_4$) and concentrated in vacuo to give a brown oil which was purified by column chromatography on silica eluting with dichloromethane containing methanol (2% up to 10%). The product-containing fractions were combined and concentrated in vacuo to give the title compound as a colourless foam, yield, 0.31 g.

Analysis %:
Found: C,71.10; H,6.84; N,9.95;
Calculated for $C_{25}H_{27}N_3O.H_2O.\tfrac{1}{4}CH_2Cl_2$: C,71.39; H,6.99; N,9.89.

$^1$H-N.M.R. (CDCl$_3$) δ=8.50 (d, 1H), 7.60 (t, 1H), 7.50-7.10 (m, 13H), 5.80-5.65 (brs, 1H), 3.75-3.60 (m, 2H), 3.30-2.80 (m, 7H), 2.45-2.25 (brm, 1H), 2.15-2.00 (m, 1H) ppm.

EXAMPLE 6

Preparation of
3-(R,S)-(1-carbamoyl-1,1-diphenylmethyl)-1-[2-(1,4-benzodioxan-6-yl)ethyl]pyrrolidine

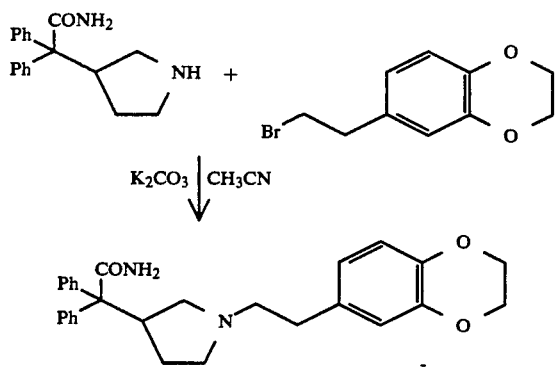

A mixture containing 3-(R,S)-(1-carbamoyl-1,1-diphenylmethyl)pyrrolidine (0.3 g-see Preparation 8), 6-(2-bromoethyl)-1,4-benzodioxan (0.26 g-see Preparation 21), anhydrous potassium carbonate (0.4 g) and acetonitrile (10 ml) was heated under reflux for 3 hours. On cooling to room temperature, water (40 ml) was added and the mixture was extracted with dichloromethane (3×30 ml). The combined dichloromethane extracts were dried (MgSO$_4$) and concentrated in vacuo to give a foam which was purified by column chromatography on silica eluting with dichloromethane containing methanol (0% up to 10%). The product-containing fractions were combined and concentrated in vacuo to give title compound as a colourless foam, yield, 0.21 g.

Analysis %:
Found: C,72.87; H,6.72; N,5.88;
Calculated for C$_{28}$H$_{30}$N$_2$O$_3$.H$_2$O: C,73.01; H,6.95; N,6.08.

$^1$H-N.M.R. (CDCl$_3$) δ=7.50-7.20 (m, 11H), 6.80-6.75 (d, 1H), 6.70-6.60 (m, 2H), 5.45-5.35 (brs, 1H), 4.25 (s, 4H), 3.60-3.45 (brs, 1H), 3.00-2.60 (m, 8H), 2.10-1.90 (m, 2H) ppm.

EXAMPLE 7

Preparation of
3-(S)-(−)-(1-carbamoyl-1,1-diphenylmethyl)-1-[2-(benzofuran-5-yl)ethyl]pyrrolidine

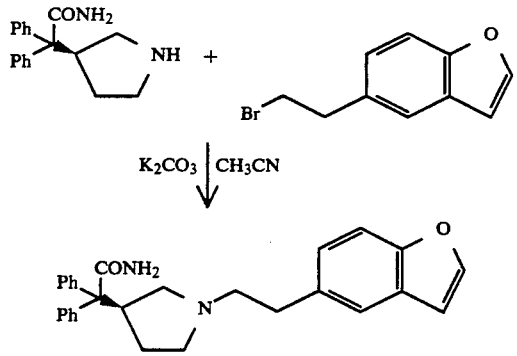

A mixture containing 3-(S)-(−)-(1-carbamoyl-1,1-diphenylmethyl)pyrrolidine (1.79 g-see Preparation 10(B)), 5-(2-bromoethyl)benzo[2,3-b]furan (1.2 g-see Preparation 17), anhydrous potassium carbonate (3 g) and acetonitrile (30 ml) was heated under reflux for 30 minutes. The mixture was partitioned between ethyl acetate (30 ml) and 10% aqueous potassium carbonate (30 ml), the layers were separated, and the aqueous layer extracted with ethyl acetate (3×50 ml). The combined ethyl acetate extracts were dried (MgSO$_4$) and concentrated in vacuo to give a brown gum which was purified by column chromatography on silica eluting with dichloromethane containing methanol (2%). The product-containing fractions were combined and concentrated in vacuo to give the title compound as a foam, yield 1.4 g.

Analysis %:
Found: C,75.65; H,6.54; N,6.25;
Calculated for C$_{28}$H$_{28}$N$_2$O$_2$.¼CH$_2$Cl$_2$: C,75.44; H,6.33; N,6.28.

$^1$H-N.M.R. (d$^6$DMSO) δ=7.85 (d, 1H), 7.45-6.90 (m, 15H), 6.80 (s, 1H), 3.65-3.50 (m, 1H), 3.35-3.20 (brm, 1H), 2.90-2.75 (m, 1H), 2.70-2.55 (m, 2H), 2.55-2.25 (m, 3H), 1.95-1.70 (m, 2H), 1.55-1.40 (m, 1H) ppm.

EXAMPLE 8

Preparation of
3-(S)-(−)-(1-carbamoyl-1,1-diphenylmethyl)-1-[2-(2,3-dihydrobenzofuran-5-yl)ethyl]pyrrolidine (Alternative to Example 1(B))

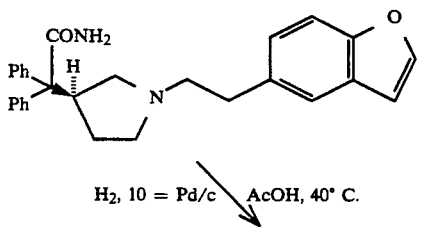

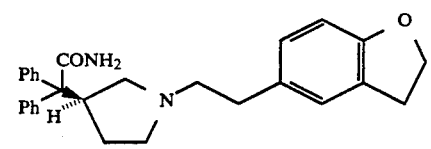

10% Palladium-on-carbon (10 mg) was added to a solution of 3-(S)-(−)-(1-carbamoyl-1,1-diphenylmethyl)-1-[2-(benzofuran-5-yl)-ethyl]pyrrolidine (0.1 g-see Example 7) in acetic acid (2 ml) and the mixture was hydrogenated at 40° C. and atmospheric pressure for 6 hours. The catalyst was filtered off and washed with water (20 ml). The combined filtrate and washings were transferred to a separating funnel, dichloromethane (20 ml) was added, and the mixture was basified by the addition of 10% aqueous sodium hydroxide. The layers were separated and the aqueous layer was further extracted with dichloromethane (3×30 ml). The combined dichloromethane extracts were dried (MgSO$_4$) and concentrated in vacuo to give a colourless solid which was purified by column chromatography on silica eluting with dichloromethane containing methanol (4%). The product-containing fractions were combined and concentrated in vacuo to give the title compound as a colourless glass, yield 0.048 g, which was characterised spectroscopically to be identical to the product of Example 1(B).

$^1$H-N.M.R. (CDCl$_3$), δ=7.50-7.20 (m, 11H); 7.00 (s, 1H); 6.90 (d, 1H); 6.70 (d, 1H); 5.45-5.30 (brs, 1H);

4.60–4.50 (t, 2H); 3.60–3.45 (m, 1H); 3.25–3.15 (t, 2H); 3.05–2.50 (m, 8H); 2.10–1.95 (m, 2H) ppm.

EXAMPLE 9

Preparation of 3-(S)-(−)-(1-carbamoyl-1,1-diphenylmethyl)-1-[2-(2,3-dihydrobenzofuran-5-yl)ethyl]pyrrolidine free base and hydrobromide (Alternative to Example 1(B) and 8)

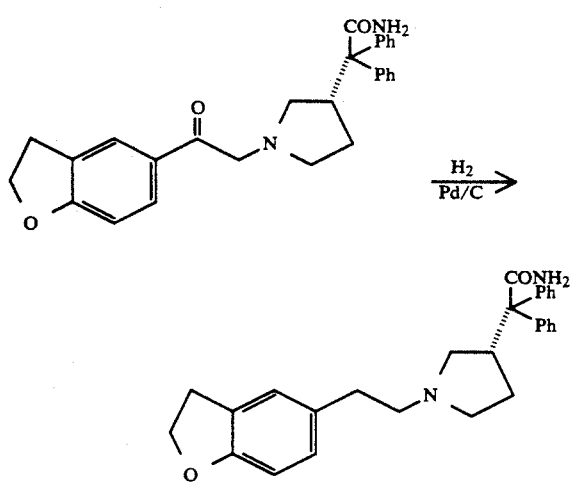

A mixture of 3-(S)-(1-carbamoyl-1,1-diphenylmethyl)-1-[2-(2,3-dihydrobenzofuran-5-yl)-2-oxoethyl]pyrrolidine hydrochloride (300 g - see Preparation 19), 5% Pd/C (30 g) and acetic acid (3000 ml) was hydrogenated at 50 psi (344.7 kPa) and 90° C. for 7 hours. The mixture was filtered and concentrated in vacuo to produce an oil which was partitioned between methylene chloride (1500 ml) and water (1500 ml). The mixture was basified with aqueous NaOH (5N), filtered to remove insolubles and the layers separated. Concentration of the organic phase in vacuo produced a crude oil which was purified by column chromatography on silica eluting with ethyl acetate containing methanol/0.880 NH4OH (10:1) from 0% to 15%. The product-containing fractions were combined and concentrated in vacuo to produce a foam, yield 171 g, of the title compound in the free base form.

The purified free base (171 g) was dissolved in acetone (855 ml) and treated with 49% aqueous HBr (66 g). The resulting precipitate was filtered off and dried to produce the title compound, yield 99.5 g, m.p. 229° C., $[\alpha]_D^{25} -30.3°$ (c=1.0, CH$_2$Cl$_2$).

Analysis %:
Found: C,66.48; H,6.29; N,5.54;
Calculated for C$_{28}$H$_{31}$N$_2$O$_2$Br: C,66.27; H,6.61; N,5.52.

$^1$H-N.M.R. (CDCl$_3$) δ=7.5–7.2 (m, 10H); 7.0 (s, 1H); 6.9 (d, 1H); 6.7 (d, 1H); 6.1–5.4 (m, 2H); 4.6–4.5 (t, 2H); 4.0–2.7 (m, 11H); 2.4–1.9 (m, 2H) ppm.

The following Preparations illustrate the preparation of certain of the starting materials used in the previous Examples.

Preparation 1

Preparation of 3-(R)-(−)-hydroxypyrrolidine hydrochloride

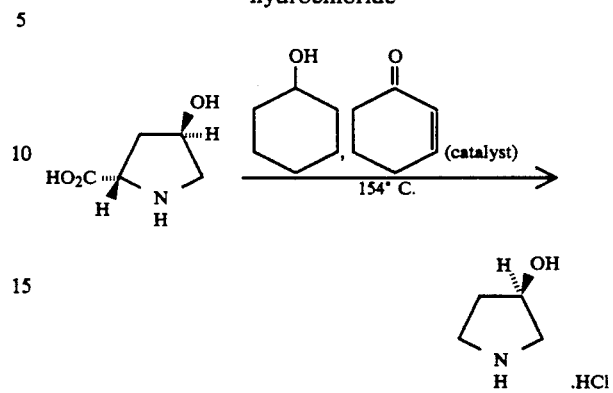

[See Chemistry Letters, 1986, 893.]

(2S,4R)-(−)-4-Hydroxy-2-pyrrolidinecarboxylic acid (40 g-commercially available), anhydrous cyclohexanol (200 ml) and 2-cyclohexen-1-one (2 ml) were heated together at 154° C. for 4.5 hours at which point the mixture was homogeneous. On cooling to room temperature, saturated ethanolic hydrochloric acid (150 ml) was added and the resulting crystalline solid was filtered off and washed with ethyl acetate (2×50 ml). The solid was recrystallised from isopropanol to give the title compound as colourless crystals, yield 19.15 g, m.p. 104°–108° C., $[\alpha]_D^{25} -8.0°$ (c 3.45, CH$_3$OH).

$^1$H N.m.r. (d$^6$DMSO), δ=10.00–8.60 (brs, 2H); 5.55–5.20 (brs, 1H); 4.40–4.25 (brs, 1H); 3.25–2.90 (m, 4H); 1.95–1.75 (m, 2H) ppm.

Preparation 2

Preparation of 1-tosyl-3-(R)-(−)-hydroxypyrrolidine

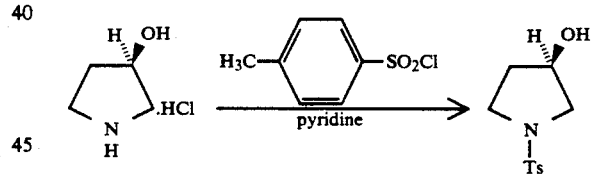

Para-toluenesulphonyl chloride (1.54 g) was added, in portions, to a solution of 3-(R)-(−)-3-hydroxypyrrolidine hydrochloride (1 g - see Preparation 1) in anhydrous pyridine (10 ml) at 0° C. The mixture was allowed to warm to room temperature and stirred for 16 hours. The solution was concentrated in vacuo and the residue was partitioned between dichloromethane (20 ml) and water (10 ml). The layers were separated and the aqueous layer was extracted with dichloromethane (2×15 ml). The combined dichloromethane extracts were washed with 2M hydrochloric acid (2×15 ml) and 10% aqueous sodium hydroxide (2×15 ml) then dried (MgSO$_4$) and concentrated in vacuo to give a solid which was recrystallised from ethanol to give the title compound as a colourless powder, yield 0.5 g, m.p. 108°–112° C., $[\alpha]_D^{25} -6.7°$ (c 1.0, CH$_2$Cl$_2$).

Analysis %:
Found: C,54.69; H,6.23; N,5.78;
Calculated for C$_{11}$H$_{15}$NO$_3$S: C,54.77; H,6.27; N,5.80.

$^1$H N.m.r. (CDCl$_3$), δ=7.80–7.70 (d, 2H); 7.40–7.30 (d, 2H); 4.45–4.35 (m, 1H); 3.50–3.35 (m, 3H); 3.30–3.25

(m, 1H); 2.45 (s, 3H); 2.05-1.80 (m, 2H); 1.75-1.70 (m, 1H) ppm.

Preparation 3

Preparation of 1-tosyl-3-(S)-(−)-tosyloxypyrrolidine

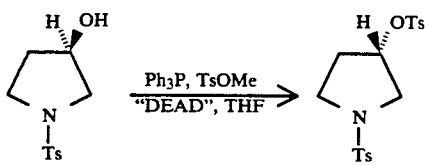

Methyl para-toluenesulphonate (54 g) was added in portions to a solution of 1-tosyl-3-(R)-(−)-hydroxypyrrolidine (49 g-see Preparation 2) and triphenylphosphine (76 g) in anhydrous tetrahydrofuran (700 ml) at 0° C. The mixture was cooled to −20° C. and diethyl azodicarboxylate (58 g-"DEAD") was added, dropwise, over 30 minutes. During this time, the temperature of the mixture was not allowed to rise above −10° C. When the addition was complete the mixture was allowed to warm to room temperature and stirred for 16 hours. The mixture was concentrated in vacuo to give a solid which was purified by column chromatography on silica eluting with hexane containing dichloromethane (50%). The product-containing fractions were combined and concentrated in vacuo to give an oil which was crystallised from 1-propanol to give the title compound as a colourless solid, yield 56 g, m.p. 110° C., $[\alpha]_D^{25} -5.2°$ (c 1.0, $CH_2Cl_2$).

Analysis %:
Found: C,54.62; H,5.46; N,3.14;
Calculated for $C_{18}H_{21}NO_5S_2$: C,54.66; H,5.35; N,3.54.

$^1H$ N.m.r. ($CDCl_3$), $\delta = 7.75-7.65$ (m, 4H); 7.40-7.30 (m, 4H); 5.00-4.90 (m, 1H); 3.55-3.35 (m, 3H); 3.30-3.20 (m, 1H); 2.50 (s, 3H); 2.45 (s, 3H); 2.10-1.90 (m, 2H) ppm.

Preparation 4

Preparation of 1-tosyl-3-(R)-(+)-tosyloxypyrrolidine

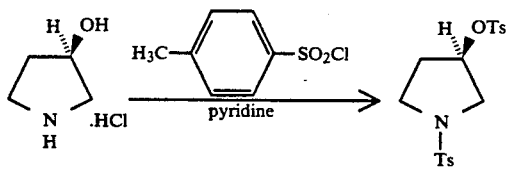

Para-toluenesulphonyl chloride (61.5 g) was added, in portions, to a solution of 3-(R)-(−)-3-hydroxypyrrolidine hydrochloride (19 g- see Preparation 1) in anhydrous pyridine (200 ml) at 0° C. The mixture was allowed to warm to room temperature and stirred for 16 hours. The solution was concentrated in vacuo and the resulting solid partitioned between dichloromethane (300 ml) and water (200 ml). The layers were separated and the aqueous layer extracted with dichloromethane (3×100 ml). The combined dichloromethane extracts were washed with 2M hydrochloric acid (2×100 ml) and 10% aqueous sodium hydroxide (2×100 ml) then dried (MgSO$_4$) and concentrated in vacuo to give an oil. Trituration with either gave a solid which was recrystallised from 1-propanol to give the title compound as a colourless solid, yield 33.5 g, m.p. 111°-112° C., $[\alpha]_D^{25} +5.3°$ (c 1.0, $CH_2Cl_2$).

Analysis %:
Found: C,54.29; H,5.39; N,3.59;
Calculated for $C_{18}H_{21}NO_5S_2$: C,54.68; H,5.35; N,3.54.

$^1H$ N.m.r. ($CDCl_3$), $\delta = 7.75-7.65$ (m, 4H); 7.40-7.30 (m, 4H); 5.00-4.90 (m, 1H); 3.55-3.35 (m, 3H); 3.30-3.20 (m, 1H); 2.50 (s, 3H); 2.45 (s, 3H); 2.10-1.90 (m, 2H) ppm.

Preparation 5

Preparation of 1-tosyl-3-(R,S)-tosyloxypyrrolidine

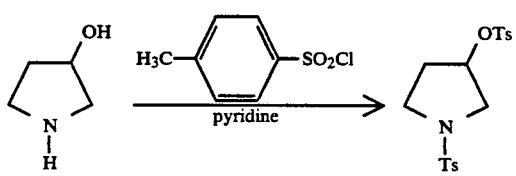

Para-toluenesulphonyl chloride (68.8 g) was added, in portions, to a solution of 3-(R,S)-hydroxypyrrolidine (15 g) in dry pyridine (200 ml) at 0° C. The mixture was allowed to warm to room temperature and stirred for 16 hours. The solution was concentrated in vacuo to approximately half the original volume then partitioned between dichloromethane (500 ml) and water (300 ml). The layers were separated and the aqueous layer was extracted with dichloromethane (3×100 ml). The combined dichloromethane extracts were washed with 2M hydrochloric acid (100 ml) and 10% aqueous sodium hydroxide (100 ml) then dried (MgSO$_4$) and concentrated in vacuo to give an oil which was crystallised from dichloromethane/ether to give the title compound as a microcrystalline powder, yield 28.3 g, m.p. 119°-121° C.

$^1H$ N.m.r. ($CDCl_3$), $\delta = 7.75-7.65$ (m, 4H); 7.40-7.30 (m, 4H); 4.95 (m, 1H); 3.55-3.35 (m, 3H); 3.30-3.20 (m, 1H); 2.50 (s, 3H); 2.45 (s, 3H); 2.10-1.90 (m, 2H) ppm.

Preparation 6

(A) Preparation of 3-(R,S)-(1-cyano-1,1-diphenylmethyl)-1-tosylpyrrolidine

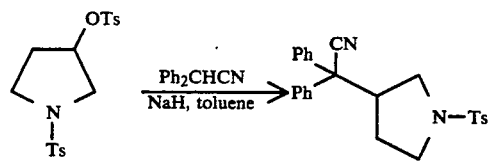

Diphenylacetonitrile (17.1 g) was added to a stirred suspension of sodium hydride (4 g of a 60% suspension in mineral oil) in anhydrous toluene (250 ml) and the mixture was heated under reflux for 2 hours. On cooling to room temperature, 1-tosyl-3-(R,S)-tosyloxypyrrolidine (28 g - see Preparation 5) was added in portions and the mixture heated under reflux for 3 hours. The mixture was diluted with toluene (150 ml), washed with 5% aqueous sodium hydroxide (2×100 ml) and brine (150 ml) then dried (MgSO$_4$) and concentrated in vacuo to give a solid which was purified by trituration with methanol to give the title compound as a colourless microcrystalline powder, yield 18 g, m.p. 186°-187° C.

$^1$H N.m.r. (CDCl$_3$), δ=7.75 (d, 2H); 7.50–7.25 (m, 12H); 3.60–3.30 (m, 4H); 3.10–3.00 (m, 1H); 2.50 (s, 3H); 2.00–1.80 (m, 2H) ppm.

(B) A similar procedure starting with 1-tosyl-3-(S)-(−)-tosyloxypyrrolidine (55 g-see Preparation 3) gave 3-(S)-(+)-(1-cyano-1,1-diphenylmethyl)-1-tosylpyrrolidine, yield 49.5 g, [α]$_D^{25}$+17.2° (c 1.0, CH$_2$Cl$_2$), m.p. 180°–185° C.

(C) A similar procedure starting with 1-tosyl-3-(R)-(+)-tosyloxypyrrolidine (33 g-see Preparation 4) gave 3-(R)-(−)-(1-cyano-1,1-diphenylmethyl)-1-tosylpyrrolidine, yield 19.7 g, m.p. 165°–78° C., [α]$_D^{25}$−17.0° (c 1.0, CH$_2$Cl$_2$).

Preparation 7

Preparation of 3-(R,S)-(1-cyano-1,1-diphenylmethyl)pyrrolidine

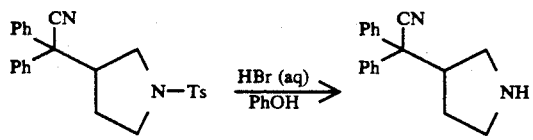

A solution of 3-(R,S)-(1-cyano-1,1-diphenylmethyl)-1-tosylpyrrolidine (21 g-see Preparation 6(A)) and phenol (21 g) in 48% aqueous hydrobromic acid (240 ml) was heated under reflux for 2 hours. The mixture was cooled to 0° C. in an ice bath and basified (pH 12) by the slow addition of 50% aqueous sodium hydroxide (280 ml). Methanol (10 ml) was added and the mixture was stirred for 15 minutes then diluted with water (300 ml). The mixture was extracted with dichloromethane (3×200 ml), the combined extracts were dried (MgSO$_4$) and concentrated in vacuo to give an oil. The oil was dissolved in 1:1 hexane/toluene (500 ml) and washed with 0.5M hydrochloric acid (3×500 ml). The aqueous extracts, together with some oil which separated during the extraction, were basified (pH 12) by the addition of aqueous sodium hydroxide (12 g in 20 ml water) and the mixture was extracted with dichloromethane (3×150 ml). The combined dichloromethane extracts were dried (MgSO$_4$) and concentrated in vacuo to give an oil which was purified by column chromatography on silica eluting with dichloromethane containing methanol (0% up to 10%). The product-containing fractions were combined and concentrated in vacuo to give the title compound as a oil, yield 10 g.

$^1$H N.m.r. (CDCl$_3$), δ=7.55–7.25 (m, 10H); 5.45 (brs, 1H); 3.55–3.40 (m, 1H); 3.35–3.10 (m, 2H); 3.05–2.90 (m, 1H); 2.65–2.40 (m, 1H); 2.10–2.00 (m, 1H); 1.95–1.80 (m, 1H) ppm.

Preparation 8

Preparation of 3-(R,S)-(1-carbamoyl-1,1-diphenylmethyl)pyrrolidine

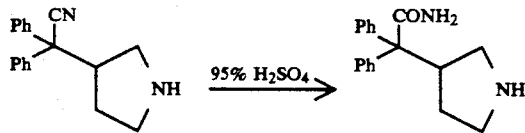

3-(R,S)-(1-Cyano-1,1-diphenylmethyl)pyrrolidine (30 g-see Preparation 7) was dissolved in 95% sulphuric acid (210 ml) and the mixture was heated, with stirring, at 85° C. for 9 hours and then at 100° C. for 30 minutes. The mixture was allowed to cool to room temperature and poured onto ice (2 kg). The mixture was basified (pH 12) by addition, in portions with cooling in an ice bath, of a cold solution of sodium hydroxide (340 g) in water (500 ml). The resulting mixture was extracted with dichloromethane (3×300 ml) and the combined extracts were dried (MgSO$_4$) and concentrated in vacuo to give the title compound as a foam, yield 16.4 g.

$^1$H N.m.r. (CDCl$_3$) δ=7.50–7.10 (m, 10H); 7.10–6.90 (brs, 0.5H); 5.90–5.30 (brm, 2.5H); 3.60–3.40 (m, 1H); 3.30–3.00 (m, 3H); 2.95–2.60 (m, 1H); 2.45–2.20 (m, 1H); 2.05–1.85 (m, 1H) ppm.

Preparation 9

(A) Preparation of 3-(S)-(+)-(1-cyano-1,1-diphenylmethyl)pyrrolidine

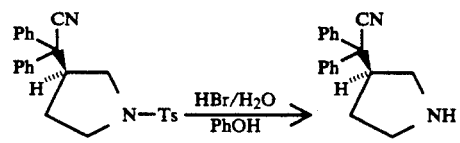

A mixture containing 3-(S)-(+)-(1-cyano-1,1-diphenylmethyl)-1-tosylpyrrolidine (49 g-see Preparation 6(B)), 48% aqueous hydrobromic acid (500 ml) and phenol (50 g) was heated under reflux for 1.25 hours then allowed to cool to room temperature. The mixture was extracted with ether (50 ml) to remove an upper layer of purple oil, then with 2:1 ether/hexane (150 ml). The aqueous layer was extracted with dichloromethane (4×100 ml), the dichloromethane extracts were combined, washed with 10% aqueous sodium hydroxide (3×50 ml), then dried (MgSO$_4$) and concentrated in vacuo to give an oil. The original ether extract was concentrated in vacuo to give an oil which was dissolved in dichloromethane (100 ml) and washed with 10% aqueous sodium hydroxide (3×50 ml). The dichloromethane solution was dried (MgSO$_4$) and concentrated in vacuo to give an oil which was combined with that obtained from the initial dichloromethane extraction. The combined oils were then dissolved in dichloromethane (200 ml) and washed with 10% aqueous sodium hydroxide solution (2×50 ml). The dichloromethane solution was dried (MgSO$_4$) and concentrated in vacuo to give an oil which was purified by column chromatography on silica eluting with dichloromethane containing methanol (0% up to 10%). The product-containing fractions were combined and concentrated in vacuo to give the title compound as a foam, yield, 24.3 g, [α]$_D^{25}$+6.0° (c 1.0, CH$_2$Cl$_2$).

Analysis %:

Found: C,78.09; H,6.70; N,9.93;

Calculated for C$_{18}$H$_{18}$N$_2$.1/5CH$_2$Cl$_2$: C,78.24; H,6.63; N,10.03.

(B) A similar procedure starting with 3-(R)-(−)-(1-cyano-1,1-diphenylmethyl)-1-tosylpyrrolidine (19.5 g-see Preparation 6(C)), gave 3-(R)-(−)-(1-cyano-1,1-diphenylmethyl)pyrrolidine, yield 9.5 g, [α]$_D^{25}$−9.8° (c 1.0, CH$_2$Cl$_2$).

Preparation 10

(A) Preparation of 3-(S)-(+)-(1-carbamoyl-1,1-diphenylmethyl)pyrrolidine L-(+)-tartrate

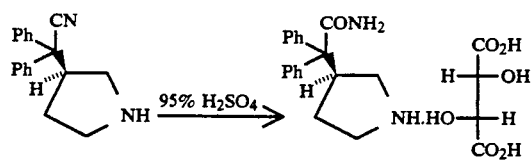

3-(S)-(+)-(1-Cyano-1,1-diphenylmethyl)pyrrolidine (24 g-see Preparation 9(A)) was dissolved in 95% sulphuric acid (210 ml) and the mixture was heated, with stirring, at 85° C. for 4.5 hours. The mixture was allowed to cool to room temperature and poured onto ice (500 g). The mixture was basified (pH 12) by the addition, in portions with cooling in an ice bath, of a cold solution of sodium hydroxide (335 g) in water (500 ml). The mixture was extracted with dichloromethane (4×200 ml) and the combined extracts were dried (MgSO4) and concentrated in vacuo to give the free base of the title compound as a colourless foam, yield 8.5 g. A portion of the foam (5.5 g) was dissolved in ethanol (50 ml) and a solution of L-(+)-tartaric acid (3 g) in warm ethanol (30 ml) was added. The resulting solid was filtered off and recrystallised from methanol to give the title L-(+)-tartrate as colourless crystals, yield, 6 g, m.p. 180°-185° C., $[\alpha]_D^{25} + 16.3°$ (c 1.0, H2O).

Analysis %:
Found: C,61.21; H,6.25; N,6.45;
Calculated for $C_{18}H_{20}N_2O.C_4H_6O_6$: C,61.38; H,6.09; N,6.51.

$^1$H N.m.r. (d$^6$DMSO), $\delta = 9.00-7.50$ (brs, 4H); 7.40-7.10 (m, 11H); 6.90-6.80 (brs, 1H); 3.90 (s, 2H); 3.90-3.70 (m, 1H); 3.50-3.35 (m, 1H); 3.25-3.00 (m, 1H); 2.75-2.60 (m, 1H); 2.55-2.40 (m, 2H); 2.15-2.00 (m, 1H); 1.40-1.30 (m, 1H) ppm.

(B) Preparation of 3-(S)-(−)-(1-carbamoyl-1,1-diphenylmethyl)pyrrolidine

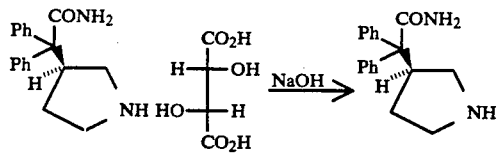

3-(S)-(+)-(1-Carbamoyl-1,1-diphenylmethyl)pyrrolidine L-(+)-tartrate from part (A) (0.95 g) was dissolved in water (40 ml) and basified (pH 12) by the dropwise addition of 10% aqueous sodium hydroxide. The mixture was extracted with dichloromethane (2×50 ml), the extracts were combined, dried (Na2SO4), and concentrated in vacuo to give the title compound as a colourless foam, yield 0.64 g.

$^1$H N.m.r. (CDCl3) $\delta = 7.50-7.20$ (m, 11H); 6.35-6.20 (brs, 1H); 5.90-5.75 (brs, 1H); 3.55-3.45 (m, 1H); 3.25-3.10 (m, 2H); 3.05-2.95 (m, 1H); 2.95-2.85 (m, 1H); 2.15-2.05 (m, 1H); 1.90-1.80 (m, 1H) ppm.

Preparation 11

Preparation of 3-(R)-(+)-(1-carbamoyl-1,1-diphenylmethyl)pyrrolidine

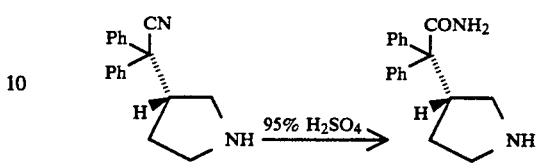

3-(R)-(−)-(1-cyano-1,1-diphenylmethyl)pyrrolidine (9.2 g-see Preparation 9(B)) was dissolved in 95% sulphuric acid (80 ml) and the mixture was heated at 80° C. for 4 hours and then at 90° C. for 1 hour. Ice (1 kg) was added and the mixture was basified (pH 12) by the addition of a cold solution of sodium hydroxide (120 g) in water (100 ml). The mixture was extracted with dichloromethane (4×100 ml) and the combined extracts were dried (MgSO4) then concentrated in vacuo to give a foam which was purified by column chromatography on alumina eluting with dichloromethane containing methanol (0% up to 10%). The product-containing fractions were combined and concentrated in vacuo to give the title compound as a foam, yield, 4.5 g, $[\alpha]_D^{25} + 16.9°$ (c 1.0, CH2Cl2).

$^1$H N.m.r. (CDCl$_o$), $\delta = 7.45-7.20$ (m, 10H); 6.10-5.90 (brs, 1H); 3.20-3.10 (m, 1H); 3.05-2.95 (m, 1H); 2.90-2.65 (m, 3H); 2.10-2.00 (m, 1H); 1.95-1.75 (m, 2H) ppm.

Preparation 12

Preparation of 5-(2-hydroxyethyl)-2,3-dihydrobenzofuran

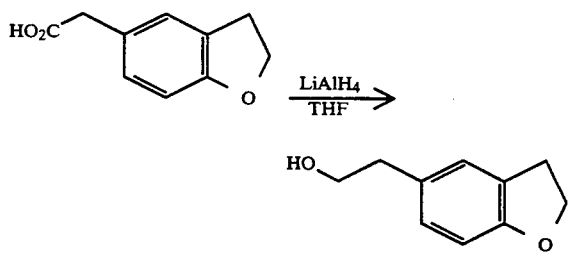

A solution of (2,3-dihydrobenzofuran-5-yl)acetic acid (4.9 g -see EP-A-132130) in anhydrous tetrahydrofuran (50 ml) was added dropwise over 10 minutes to a stirred suspension of lithium aluminium hydride (1.57 g) in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide (1.5 ml) and, finally, water (4.5 ml). The mixture was filtered and the inorganic salts washed with ethyl acetate (2×50 ml). The filtrate and washings were combined and concentrated in vacuo to give the title compound as an oil, yield 3.3 g.

$^1$H N.m.r. (CDCl3) $\delta = 7.10$ (s, 1H); 7.00 (d, 1H); 6.75 (m, 1H); 4.65-4.55 (m, 2H); 3.90-3.75 (m, 2H); 3.30-3.15 (m, 2H); 2.90-2.80 (m, 2H); 1.85-1.75 (brs, 1H) ppm.

Preparation 13

Preparation of 5-(2-bromoethyl)-2,3-dihydrobenzofuran

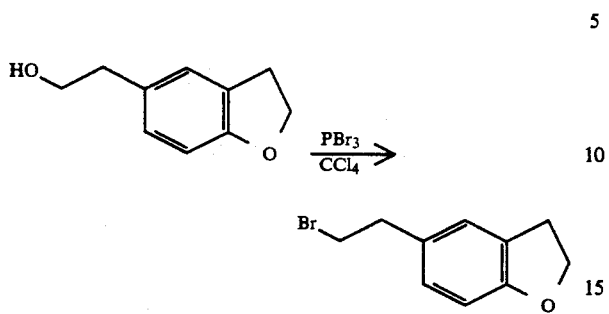

Phosphorus tribromide (0.37 g) was added to a solution of 5-(2-hydroxyethyl)-2,3-dihydrobenzofuran (0.612 g-see Preparation 12) in carbon tetrachloride (3ml) and the mixture was heated under reflux for 3 hours. On cooling to room temperature, the mixture was partitioned between 10% aqueous sodium carbonate (20 ml) and dichloromethane (20 ml). The layers were separated and the aqueous layer was extracted with dichloromethane (2×10 ml). The combined dichloromethane extracts were dried (MgSO$_4$) and concentrated in vacuo to give the title compound as an oil which crystallised on standing, yield 0.584 g, m.p. 60°-62° C.

$^1$H N.m.r. (CDCl$_3$) δ=7.10 (s, 1H); 7.00-6.95 (d, 1H); 6.80-6.70 (d, 1H); 4.65-4.55 (t, 2H); 3.60-3.50 (t, 2H); 3.25-3.15 (t, 2H); 3.15-3.10 (t, 2H) ppm.

Preparation 14

Preparation of 5-(2-bromoethyl)indane

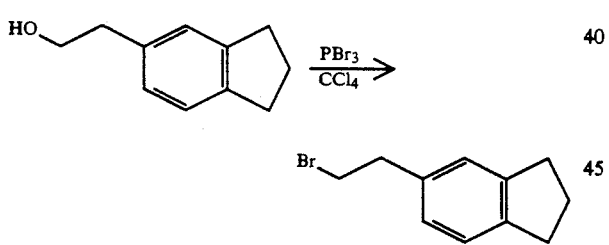

Phosphorus tribromide (3.5 ml) was added, dropwise, to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate. The layers were separated and the aqueous layer extracted with dichloromethane (2×100 ml). The combined dichloromethane extracts were dried (MgSO$_4$) and concentrated in vacuo to give an oil which was purified by column chromatography on silica eluting with dichloromethane. The product-containing fractions were combined and concentrated in vacuo to give the title compound as a colourless oil, yield 10.5 g.

$^1$H N.m.r. (CDCl$_3$) δ=7.30-7.00 (m, 3H); 3.60 (m, 2H); 3.20 (m, 2H); 3.00-2.85 (m, 4E); 2.20-2.05 (m, 2H) ppm.

Preparation 15

3,4-Methylenedioxyphenethyl alcohol

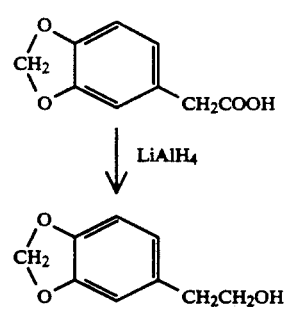

3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at room temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.01 g, 90%), which was characterised by its $^1$H n.m.r. spectrum.

$^1$H N.m.r. (CDCl$_3$) δ=6.69-6.83 (3H, m); 5.98 (2H, s); 3.82 (2H, dt, J=7 and 6 Hz); 2.81 (2H, t, J=7 Hz) and 1.44 (1H, t, J=6 Hz, exchangeable with D$_2$O).

Preparation 16

3,4-Methylenedioxyphenethyl bromide

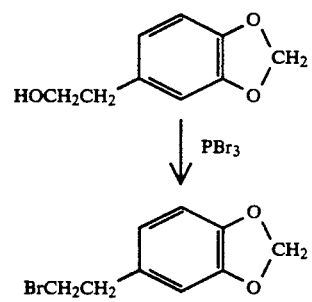

A solution of phosphorus tribromide (8.1 g) in carbon tetrachloride (50 ml) was added dropwise over 30 minutes to a stirred solution of 3,4-methylenedioxyphenethyl alcohol (15.0 g) (see Preparation 15) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatogrpahy on silica (100 g) using carbon tetrachloride as the eluant. Appropriate fractions were combined and evaporated to give the title compound as a pale yellow oil (8.3 g, 40%), which was characterised by its $^1$H n.m.r. spectrum.

$^1$H N.m.r. (CDCl$_3$) δ=6.80 (1H, d, J=8 Hz), 6.75 (1H, s); 6.71 (1H, d, J=8 Hz); 6.00 (2H, s); 3.56 (2H, t, J=7 Hz) and 3.13 (2H, t, J=7 Hz).

Preparation 17

Preparation of 5-(2-bromoethyl)benzo[2,3-b]furan

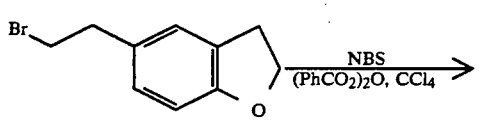

A mixture containing 5-(2-bromoethyl)-2,3-dihydrobenzo-[2,3-b]furan (3 g-see Preparation 13), freshly recrystallised N-bromosuccinimide (2.37 g), benzoyl peroxide (0.03 g) and carbon tetrachloride was heated under reflux for 2 hours. On cooling to room temperature, water (100 ml) and sodium metabisulphite (1 g) were added, the layers were separated and the aqueous layer was extracted with dichloromethane (3×50 ml). The combined organic extracts were dried (MgSO$_4$) and concentrated in vacuo to give an oil which was purified by column chromatography on silica eluting with hexane containing toluene (5%). The product-containing fractions were combined and concentrated in vacuo to give the title compound as an oil, yield 1.25 g.

$^1$H-N.M.R. (CDCl$_3$) δ=7.70 (d, 1H), 7.55-7.45 (m, 2H), 7.25-7.15 (d, 1H), 6.80 (s, 1H), 3.70-3.60 (t, 2H), 3.35-3.25 (t, 2H) ppm.

Preparation 18

Preparation of 5-chloroacetyl-2,3-dihydrobenzofuran

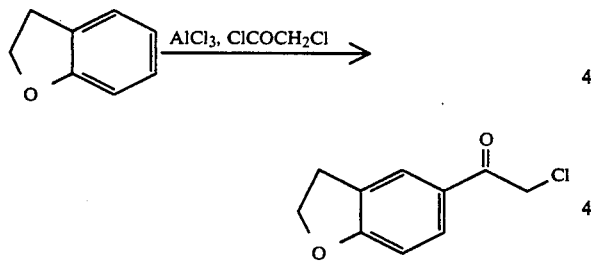

Chloroacetyl chloride (10.39 g) was dissolved in methylene chloride (25 ml) and the solution was added to a slurry of aluminium chloride (12.2 g) in methylene chloride (50 ml) at −15° C. A solution of dihydrobenzofuran (10 g) in methylene chloride (25 ml) was added and the solution was allowed to warm to room temperature over 20 hours. The reaction mixture was poured into ice (700 g) and the aqueous layer was back-washed with methylene chloride (2×200 ml). The combined organic extracts were washed with water (800 ml), dried with MgSO$_4$ and concentrated in vacuo. The resulting solid (11 g) was heated in cyclohexane (110 ml) and the supernatant liquid decanted off and allowed to crystallise. Filtration produced the title compound as a white solid, yield 2.1 g, m.p. 85°-87° C.

Analysis %:
Found: C,60.75; H,4.67;
Calculated for C$_{10}$H$_9$ClO$_2$: C,61.08; H,4.61.

$^1$H-N.M.R. (CDCl$_3$) δ=7.9 (s, 1H); 7.8 (d, 1H); 6.85 (d, 1H); 4.7 (t, 2H); 4.65 (s, 2H); 3.3 (t, 2H) ppm.

Preparation 19

Preparation of 3-(S)-(1-carbamoyl-1,1-diphenylmethyl)-1-[2-(2,3-dihydrobenzofuran-5-yl)-2-oxoethyl]pyrrolidine hydrochloride

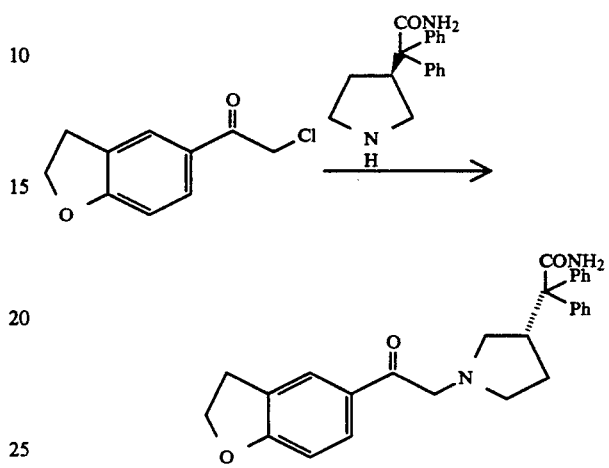

A mixture of 5-chloroacetyl-2,3-dihydrobenzofuran (176.2 g-see Preparation 18), 3-(S)-(−)-(1-carbamoyl-1,1-diphenylmethyl)pyrrolidine (335.0 g-see Preparation 10(B)) and potassium carbonate (335 g) were stirred in industrial methylated spirits at room temperature for 18 hours then concentrated in vacuo. The oily solid was partitioned between methylene chloride (2,500 ml) and water (2,500 ml) and the organic phase was concentrated to an oil in vacuo. The oil was dissolved in ethyl acetate (3,350 ml) and acidified with hydrochloric acid dissolved in isopropyl alcohol (180.6 ml at 24% w/v). Filtration produced the title compound as a hygroscopic solid, yield 467 g.

This material was used directly in Example 9 without further purification.

Preparation 20

6-(2-Hydroxyethyl)-1,4-benzodioxan

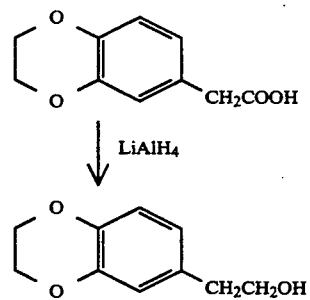

This was prepared as described in Preparation 15 using (benzodioxan-6-yl)acetic acid instead of 3,4-methylenedioxyphenylacetic acid. The title compound was obtained as a colourless oil (19.8 g, 92%), which was characterized by its $^1$H-n.m.r. spectrum.

$^1$H-N.M.R. (CDCl$_3$) δ=6.84 (1H, d, J=8 Hz); 6.77 (1H, d, J=2 Hz); 6.73 (1H, dd, J=8 and 2 Hz); 4.28 (4H, s); 3.59 (2H, t, J=7 Hz) and 3.08 (2H, t, J=7 Hz).

Preparation 21

6-(2-Bromoethyl)-1,4-benzodioxan

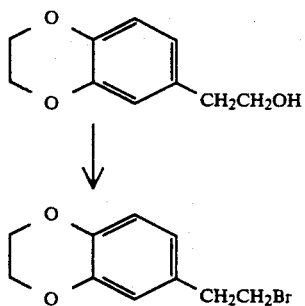

This was prepared as described in Preparation 16 using 6-(2-hydroxyethyl)-1,4-benzodioxan (see Preparation 20) instead of 3,4-methylenedioxyphenethyl alcohol. The title compound was obtained as a pale yellow oil (21.4 g, 80%), which was characterized by its $^1$H-N.M.R. spectrum.

$^1$H-N.M.R. (CDCl$_3$) δ=6.83 (1H, d, J=8 Hz); 6.77 (1H, d, J=2 Hz); 6.72 (1H, dd, J=8 and 2 Hz); 4.28 (4H, s); 3.59 (2H, t, J=7 Hz) and 3.10 (2H, t, J=7 Hz).

The compounds of the Examples have all been found to have useful activity as selective muscarinic receptor antagonists without significant adverse toxicity.

We claim:

1. A compound of the formula:

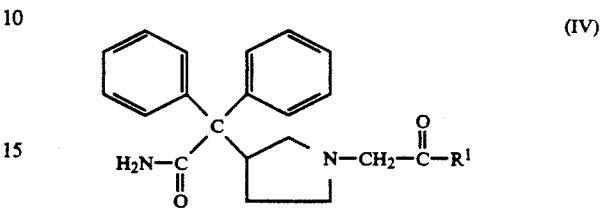

(IV)

where R$^1$ is 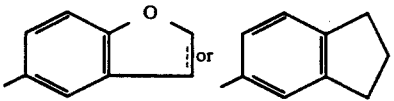

where the dotted line is an optional bond.

* * * * *